United States Patent [19]

Liu

[11] Patent Number: 4,684,628

[45] Date of Patent: Aug. 4, 1987

[54] PHARMACEUTICAL COMPOSITION CONTAINING PURE SAN-MAI-SEN

[76] Inventor: Yaguang Liu, 67-08, 168th St., Flushing, N.Y. 11365

[21] Appl. No.: 730,365

[22] Filed: May 3, 1985

[51] Int. Cl.$^4$ .................. A61K 31/705; A61K 31/045
[52] U.S. Cl. ...................................... 514/26; 514/739; 514/824; 514/885
[58] Field of Search ............... 424/195.1; 514/182, 514/26, 739, 824, 885

[56] References Cited

U.S. PATENT DOCUMENTS 4,103,033 7/1978 Thomas .............................. 514/739
4,317,816 3/1982 Arichi et al. ........................ 514/26

FOREIGN PATENT DOCUMENTS 0163322 9/1984 Japan ......................................... 26/

OTHER PUBLICATIONS

Chem Abst. 78(15): 92672q, 1973.
Chem Abst. 82(20): 129206u, 1975.
Lewis, Med. Botary, Wiley & Sons, N.Y., pp. 372, 373, 1977.

*Primary Examiner*—Johnnie R. Brown
*Assistant Examiner*—John W. Rollers, Jr.
*Attorney, Agent, or Firm*—Chenpatents

[57] ABSTRACT

A new pharmaceutical composition for treatment and prevention of cardiovascular disease, and increasing immune function contains Ginsenoside, Ophiopogonin, Sesquicarene and Chamigrene. Processes for producing these components and the composition, referred to as Pure San-Mai-Sen (PSMS), are provided.

2 Claims, No Drawings

PHARMACEUTICAL COMPOSITION CONTAINING PURE SAN-MAI-SEN

BACKGROUND OF THE INVENTION

1. Field of the Invention

This invention relates to a new pharmaceutical composition for treatment and prevention of cardiovascular disease, and increasing the immune function.

Specifically, this invention provides a new composition of four major active ingredients: Ginsenoside, Ophiopogonin, Sesquicarene and Chamigrene.

2. Description of Prior Art

Ginseng roots have long been used in Asia to prepare drugs and medicines. Many methods of extracting the active ingredients of ginseng roots have been used over the years including stewing, or extraction with solvents such as ethanol.

SUMMARY OF THE INVENTION

There is a need to provide a composition comprising several active ingredients which, in combination, are useful in treating and preventing cardiovascular disease in the human body and in increasing resistance to infection (immune response). This invention provides a pharmaceutical composition referred to as Pure San-Mai-Sen (PSMS) where Sen-Mai-Sen is a transliteration of the Chinese name for medicine, and a process for preparing the same. PSMS comprises Ginsenoside (I), Ophiopogonin (II), Sesquicarene (III) and Chamigrene (IV), all of which are derived from plant materials. The approximate composition of PSMS and the sources of its components are listed below:

TABLE 1

| Component | source | Approximate Concentration in Weight Percent in PSMS |
| --- | --- | --- |
| Ginsenoside (I) | Roots of *Panax quinquefolium* L, or *Panax ginseng* C. A. Mey, generally referred to as ginseng | 25–60 |
| Ophiopogonin (II) | *Ophiopogon japonica* Ker-Gawl | 25–60 |
| Sesquicarene (III) and Chamigrene (IV) | *Schisandra chinensis* Baill | 5–50 |

The process for producing PSMS comprises extracting ground of the above natural materials with appropriate solvents such as alcohol or water, removing lipids by extraction with ether where necessary, vacuum-distilling the extracts with and without addition of butanol, and preparing PSMS by mixing its components in the desired proportion.

BRIEF DESCRIPTION OF THE CHEMICAL STRUCTURE FORMULAE

The chemical structures of the components of PSMS are shown in Formulae 1–5.

Ginsenoside (I) is a mixture of Ginsenoside b, and g, as illustrated in Formulae 1 and 2.

Ophiopogonin (II) is a mixture of Ophiopogonin B and D as illustrated in Formula 3.

Sesquicarene (III) and Chamigrene (IV) are isomers occurring in a mixture. Their structures are illustrated in Formulae 4 and 5.

PSMS is produced by mixing the above components in the proportions given in Table 1 above.

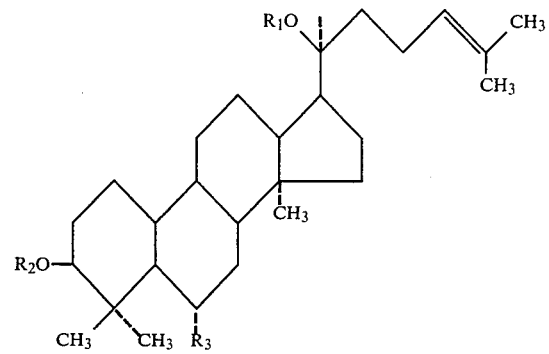

When $R_1$ = Glucose $\underline{6\ 1}$ Glucose $R_2$ = Glucose $\underline{2\ 1}$ Glucose $R_3$ = H the compound is Ginsenoside $b_1$. Melting Point, 198–202° C.

When $R_1$ = Glucose $R_2$ = H $R_3$ = —O—Glucose-Rhamnose the compound is Ginsenoside $g_1$. Melting Point, 192–194° C.

Formula 1 Chemical structure of Ginsenoside (I)

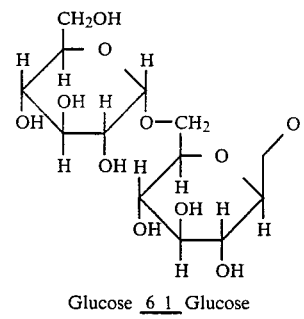

Glucose $\underline{6\ 1}$ Glucose

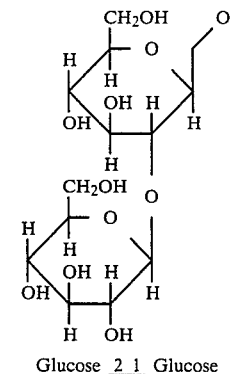

Glucose $\underline{2\ 1}$ Glucose

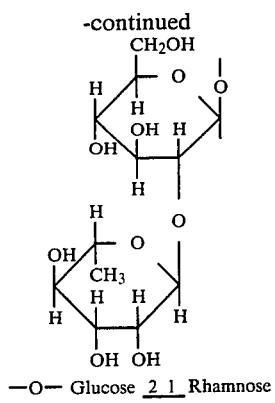

—O— Glucose $\underline{2\ 1}$ Rhamnose

Formula 2 Chemical Structure of Substituents of Ginsenoside

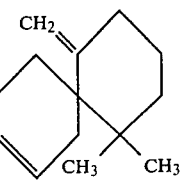

Formula 5. Chemical Structure of Chamigrene (IV)

DETAILED DESCRIPTION

The processes for producing the above-mentioned active ingredients of PSMS are described by the following examples:

EXAMPLE 1

Extraction and Purification of Ginsenoside 1000 gms. of dried ginseng powder is extracted with 2000 ml of 95% ethanol at room temperature for 24 hours. The powder is recovered by filtration. Filtrate A is saved and the powder filtercake is refluxed with an additional 2000 ml of 95% ethanol on a steam bath. The mixture is filtered again. Filtrate B is saved and the powder filtercake is refluxed two more times for 6 hours with additional 2000 ml batches of 95% ethanol and filtered, providing filtrates C and D. Filtrates A, B, C, and D are combined and distilled at 17 mm Hg absolute, whereby ethanol is recovered and a still residue is obtained.

This still residue is dissolved in 500 ml of distilled water. This water solution is extracted five times with 500 ml of a lipophilic solvent, e.g. diethyl ether or petroleum ether, whereby lipids are removed from the solution.

To this aqueous raffinate is added 500 ml of water-saturated n-butanol and the mixture is distilled at 17 mm

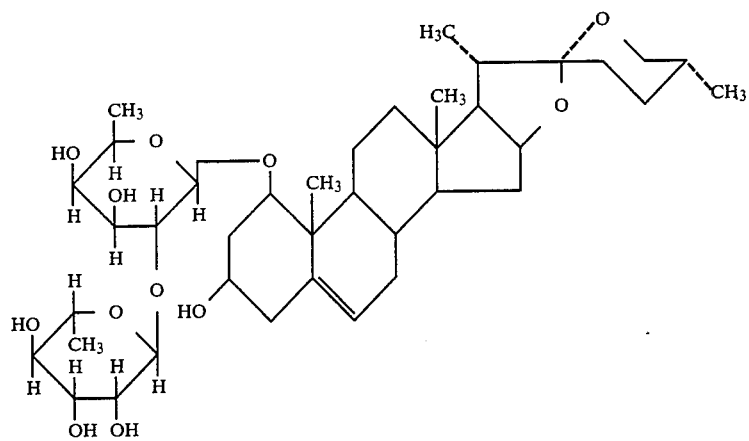

When R = H the component is Ophiopogonin B, which has a melting point of 269-271° C.

When R = as following chemical structure

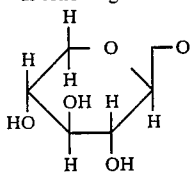

the component is Ophiopogonin D, which has a melting point of 263-265° C.

Formula 3. Chemical Structure of Ophiopogonin (II)

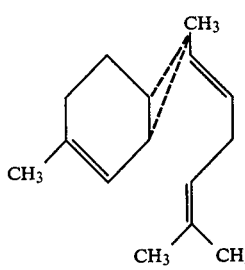

Formula 4. Chemical Structure of Sesquicarene (III)

Hg absolute to dryness, whereby a powder residue is obtained. This powder is dissolved in 500 ml of anhydrous ethanol, and 2000 ml of acetone are added with agitation while a precipitate forms. The precipitate is recovered by filtration and washed twice with acetone and twice with diethyl ether and dried. About 60 gms. of a white to light yellow powder are recovered. This is Ginsenoside (I).

EXAMPLE 2

Extraction and Purification of Ophiopogonin 1000 gms. of Ophiopogon japonica Ker-Gawl powder are soaked in 2000 ml of 75% ethanol at room temperature for 24 hours. The mixture is filtered and the filtercake powder is refluxed twice for two hours with 2000 ml of 75% ethanol and filtered.

The filtrates are combined and distilled on a steam bath at 17 mm Hg absolute, whereby wet ethanol is evaporated and an aqueous still residue is obtained. This still residue is extracted with 500 ml of diethyl ether four times to remove lipids. Other solvents such as petroleum ether may be used.

To this aqueous raffinate are added 500 ml of n-butanol and the mixture is evaporated to dryness at 17 mm Hg absolute, whereby about 30 gms. of powder residue are obtained. This is Ophiopogonin (II).

EXAMPLE 3

Recovery of Sequicarene/Chamigrene 1000 gms. of *Schisandra chinensis* Baill is ground into powder and added to 2000 ml of distilled water. The mixture is vacuum-distilled and the distillate fraction recovered at 10 mm Hg absolute between 80° and 130° C. is separated. About 14 gms. of this distillate are obtained. It contains the isomers, Sesquicarene (III) and Chamigrene (IV).

EXAMPLE 4

Preparation of PSMS Liquid 120 gms. of Ginsenoside, 90 gms. of Ophiopogonin, and 28 gms. of Sequicarene/Chamigrene are dispersed and dissolved in 500 ml of distilled water. The pH of this solution is adjusted to 7 by addition of dilute hydrochloric acid. This is PSMS Liquid.

On a dry basis, the composition of PSMS may vary as follows:

|  | Weight percent | Preferred composition weight percent |
| --- | --- | --- |
| Ginsenoside | 25–60 | 25 |
| Ophiopogonin | 25–60 | 50 |
| Sesquicarene/Chamigrene | 5–50 | 25 |

The dry ingredients of PSMS, prepared in accordance with the present invention, may be incorporated in tablets, capsules and syrups by conventional methods which are not part of this invention.

This invention will now be described with reference to its beneficial effects, as illustrated by the following tests:

EXAMPLE 5

The influence of PSMS on the survival rate of myocardial cells in a low nutrition medium Culture of chick heart cell. Hearts were removed from embryos and were dissociated at 37° C. for 45 minutes with 0.25% trypsin (sigma, type III), 0.025% collagenase (sigma, type I), and 0.005% pancreatin (NBCo) prepared in calcium and magnesium-free saline G containing 4% chicken serum. Then the tissue is dispersed into a single cell suspension in culture medium containing 5 mg/ml DNAse I (sigma). Viable cell counts were determined by hemocytometer counting. Cells were dispersed into 60 mm culture dishes (surface area 2000 mm$^2$) at densities of 200 cells/mm$^2$.

Cultures were maintained in Ham's F-12K cln$^-$ a medium for myocardial cells as described in Kaighn, ME "Tissue Culture, Method and Application," (Kruse and Patterson, eds.) pg. 54–58, Academic Press, 1973, and supplemented with 5% fetal bovine serum, gentamicin (5 mg/100 ml). Tissue culture plates were incubated under 5% $CO_2$ and 95% air at 37° C.

All cells were counted in 20 randomly selected field across the entire dish. A Zeiss microscope 25X objective having a field of view of 0.32 mm$^2$ was used for cell counting. In a low nutrition culture medium, chick myocardial cells take longer, for example 7 days, for some of the cells to die. Therefore the number of cells decreases. Under similar condition PSMS at 150 mg/ml increases the number of chick myocardial cells (Table 1).

Chick myocardial cells were divided into 3 groups after being put into culture for 1 day under normal condition. 100% nutrition group is the normal medium, twice a week the medium was changed. The 10% nutrition group uses a 10% medium and 90% physiological saline solution. The medium and physiological saline solution was not changed for a week. The PSMS group is 10% medium and 90% of 150 µg/ml of PSMS. The medium is not changed for a week. On the seven (7th) day, the cell counts were as follows:

| Number of chick myocardial cells | | |
| --- | --- | --- |
| 100% nutrition | 10% nutrition | PSMS + 10% nutrition |
| 90.0 ± 5.4 (*3) | 25.1 ± 3.6 (*10) | 54.9 ± 14.4 (*9) $p < 0.05$ |

*indicates number of samples

EXAMPLE 6

The influence of PSMS on the Autoradiograms of myocardial cells in a low nutrition medium Autoradiograms-cellular labelling was conducted in medium prepared without unlabelled thymidine and containing 5 µci/ml methyl-$^3$H-thymidine (New England Nuclear) at a specific activity of 50.8 Ci/mole. Cultures were labelled in medium containing $^3$H-thymidine labelling. After labelling, plates were rinsed in saline, fixed in formalin: ethanol (1:9), stained with periodic acid-schiff (PAS) and coated with Kodak NTB-3 emulsion, a nuclear emulsion diluted 1:1 with water. Autoradiograms were exposed for 7 days then developed in Dektol counterstained with 1% aqueous fast green and air dried.

At least 1000 nuclei per culture were counted at random, cells having more than 50 silver grains over the nucleus were scored as positive labelling, background was usually less than 5 grains. The cellular density of each culture was also determined by recording the number of microscopic fields counted to assess the total area scored. A Zeiss 25X objective having a field of view of 0.32 mm² was used for cell counting.

Under similar condition described in Table 1, experiment of Autoradiograms was performed. From Table 2 we can see PSMS at 150 µg/ml can increase percentage of myocardial cell nuclei labelled. That is PSMS increases DNA synthesis of chick myocardial cells.

| Percent of myocardial cell nuclei labelled | | |
|---|---|---|
| 100% nutrition | 10% nutrition | 10% nutrition + PSMS |
| 19.0 ± 1.2 (*3) | 11.5 ± 1.6 (*7) | 17.0 ± 2.3 (*7) $P < 0.01$ |

*indicates number of samples

EXAMPLE 7

The influence of PSMS on the cardiovascular experiment in animals

Cardiovascular experiments are carried out in accordance with procedures outlined in: Kirby, M. L. Journal of Molecular and Cellular Cardiology (1983) 15 (10) : 685.

The above three compounds in animal experiments reflect the following results:

A. PSMS can significantly increase myocardial DNA synthesis; treated group/control group=365.7%, $P<0.001$.

B. PSMS can prolong significantly the survival time of mice under hypoxia. Survival time in minutes of the control group is 10±5 min. PSMS group is 56±3 min., $P<0.001$ ($O_2$ about 5%)

C. PSMS can enhance markedly the coronary flow on isolated perfused hearts. Drug group/control group=183.69%. Myocardial uptake of $^{86}Pb$ was raised in rats.

EXAMPLE 8

The influence of PSMS on the immune function in animals

A. PSMS caused markedly increase lymphocytoblastogenesis. Mice were injected with acetoprednisolone making up a model of inhibited immunity, then establishing the index of stimulation of lymphocyto blastogenesis.

control group: 16.87
PSMS group: 30.12 ($P<0.001$).

B. PSMS caused increase of serum complement content in guinea pigs.

control group: 301 µ/ml
PSMS group: 359 µ/ml ($P<0.05$).

C. PSMS was found to markedly increase the formation of roset in guinea pigs.

control group: 42.7%
PSMS group: 65.3% ($P<0.01$).

D. PSMS could increase the content of serum lysozyme in mice.

control group: 9.0 µg/ml
PSMS group: 11.7 µg/ml ($P<0.01$).

EXAMPLE 9

Toxicity of PSMS

A. The toxicity of PSMS in human body and animal was found to by very low. When PSMS was administered orally to mice at a dose of 48 g/Kg neither death nor toxic effect was observed other than a sedative appearance.

B. $LD_{50}$: 1295 mg/Kg injection in abdominal cavity in mice.

C. Each dose for an adult is 20 mg. Using 50 Kg as the average weight of an adult the dosage is 0.4 mg/Kg, therefore it is very safe.

The embodiment of the invention described here can be modified within the spirit and scope of the present invention. Numerous modifications and variations of the present invention are possible in light of the above teachings.

Having described a pharmaceutical composition referred to as PSMS, a process for producing PSMS, and furthermore described its effect on cardiovascular disease as well as other effects studied by tests carried out by approved procefures.

I claim:

1. A pharmaceutical composition for treatment of cardiovascular disease and increasing immunity, comprising, in weight percent, ginsenoside, 25-60%; ophiopogonin, 25-60%; and sesquicarene/chamigrene, 5-50%.

2. A method for treatment of cardiovascular disease and for increasing immunity in a human, in need thereof, comprising administering to said human an effective dose of a pharmaceutical composition of claim 1.

* * * * *